United States Patent
Witte

(10) Patent No.: US 7,677,275 B2
(45) Date of Patent: Mar. 16, 2010

(54) ONE HAND SYRINGE FILLING DEVICE

(76) Inventor: John Witte, 118 Northwood, Lexington, KY (US) 40505

( * ) Notice: Subject to any disclaimer, the term of this patent is extended or adjusted under 35 U.S.C. 154(b) by 347 days.

(21) Appl. No.: 11/503,432

(22) Filed: Aug. 14, 2006

(65) Prior Publication Data

US 2008/0065024 A1 Mar. 13, 2008

(51) Int. Cl.
B65B 3/04 (2006.01)
A61M 5/00 (2006.01)

(52) U.S. Cl. .................. 141/27; 141/330; 141/383; 604/414

(58) Field of Classification Search ............. 141/27, 141/329, 330, 383; 604/411–415
See application file for complete search history.

(56) References Cited

U.S. PATENT DOCUMENTS

| | | | | |
|---|---|---|---|---|
| 2,677,372 A | * | 5/1954 | Barnish, Jr. .............. 604/414 |
| 3,602,272 A | * | 8/1971 | Stawski .................... 141/27 |
| 3,833,030 A | * | 9/1974 | Waldbauer et al. .......... 141/26 |
| 3,853,158 A | * | 12/1974 | Whitty ..................... 141/27 |
| 3,875,979 A | * | 4/1975 | Hults ....................... 141/27 |
| 4,196,732 A | | 4/1980 | Wardlaw |
| 4,252,159 A | * | 2/1981 | Maki ....................... 141/27 |
| 4,316,558 A | * | 2/1982 | Kubiak ..................... 141/27 |
| 5,037,390 A | * | 8/1991 | Raines et al. .............. 604/83 |
| 5,487,738 A | * | 1/1996 | Sciulli ..................... 141/27 |
| 5,494,087 A | * | 2/1996 | Pitelka et al. .............. 141/27 |
| 5,542,760 A | | 8/1996 | Chanoch et al. |
| 5,692,642 A | | 12/1997 | Brattesani |
| 5,873,859 A | * | 2/1999 | Muntz ..................... 141/27 |
| 6,006,798 A | * | 12/1999 | Lindquist ................. 141/27 |
| 6,439,276 B1 | * | 8/2002 | Wood et al. ............... 141/27 |
| 2001/0018937 A1 | * | 9/2001 | Nemoto .................... 141/27 |
| 2002/0124905 A1 | * | 9/2002 | Draughn et al. ........... 141/329 |

* cited by examiner

Primary Examiner—Gregory L Huson
Assistant Examiner—Nicolas A Arnett
(74) Attorney, Agent, or Firm—Michael Coblenz

(57) ABSTRACT

A device and method for easily filling a syringe with one hand is disclosed. The device includes a flat hand for holding a medicine bottle, a syringe holder with a curved finger for holding a syringe, a mounted post for securing the device and a swivel arm mounted to the post which holds the flat hand, wherein the swivel arm allows the user to invert the flat hand and the medicine bottle secured therein, and easily draw medicine from the medicine bottle into the syringe with one hand.

8 Claims, 4 Drawing Sheets

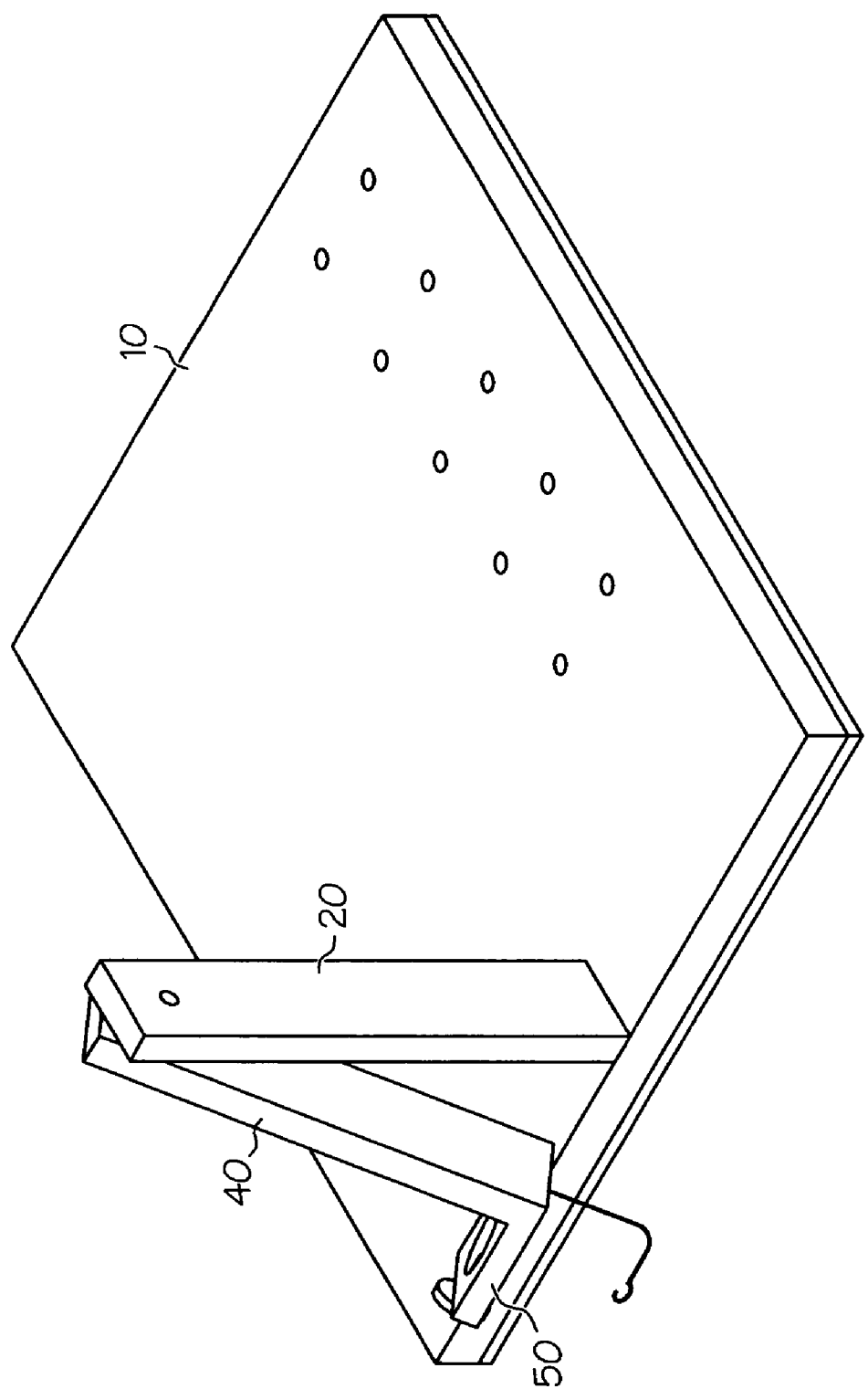

ONE HAND SYRINGE FILLING DEVICE

CROSS REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to a device and method for filling a syringe or hypodermic needle. More specifically, the invention allows for the filling of a syringe with one hand.

2. Description of the Related Art

Many people receive liquid medicine by injection from a syringe or hypodermic needle. Use of a syringe or hypodermic needle to inject liquid medicine is well known in the medical arts. In many cases, people have to inject themselves, and some people have to inject themselves frequently, even multiple times per day. This is particularly true of diabetics, who have to give themselves frequent shots of insulin to maintain proper blood sugar levels. But it is also true of other people with other medical needs.

Use of syringes to inject medicine is well known in the art and is described here only to explain the use of the invention. Standard medicine bottles holding liquid medicine have a rubber membrane or Elastomeric seal at the top of the bottle, and medicine is removed from the bottle to inject into the patient by means of a syringe or hypodermic needle that is inserted into the medicine bottle through the Elastomeric seal. A syringe is made up of three parts: the barrel, the plunger and the needle. To remove liquid medicine with a syringe from a standard medicine bottle, the user will hold the bottle of medicine in one hand and the syringe in the other hand. The needle of the syringe will be stabbed into the top of the bottle through the Elastomeric seal, then the bottle and syringe are inverted, with the user holding the bottle in the palm of the hand while securing the syringe with the fingers of the same hand. The medicine is removed by pulling down on the plunger, away from the medicine bottle, with the other hand, which creates a vacuum inside the barrel of the syringe that pulls the medicine into the syringe.

Typically, the syringe is filled with more than the desired amount of medicine and the excess is squirted back into the medicine bottle by pushing the plunger. With the bottle inverted and the syringe held upright, any air will go to the top of the barrel of the syringe. This air is removed from the syringe by pressing the plunger. The process of filling a syringe can be easily mastered with two hands, but as can be appreciated, this process will be exceedingly difficult, if not impossible, to do with only one hand.

In many cases, the elderly and people with medical needs have limited mobility, limited dexterity, and limited use of hands or arms. This is particularly true of diabetics, who often have problems with manual dexterity as well as vision loss due to the effects of the disease, and occasionally lose use of an appendage due to the ravages of the disease. In some extreme cases arms and legs are amputated. But there are a variety of medical conditions, as well as birth defects and accidents that can limit the use of a hand or an arm. It is particularly difficult for a person with the use of only one hand or arm to prepare a hypodermic needle to inject themselves.

There is a need, therefore, for a device that allows a person to prepare and fill a syringe or prepare a hypodermic needle with the use of one hand.

BRIEF SUMMARY OF THE INVENTION

The invention relates to a device and method for filling a syringe or hypodermic needle. The device includes a flat hand for holding a medicine bottle, a syringe holder with a curved finger for holding a syringe, a mounted post for securing the device and a swivel arm mounted to the post which holds the flat hand, wherein the swivel arm allows the user to invert the flat hand and the medicine bottle secured therein, and draw medicine from the medicine bottle into the syringe.

The invention also includes a base for setting the device on a horizontal surface, and a bottle recess with set screw within the flat hand for securing the medicine bottle into the flat hand. Additionally, the invention contains a hinge that allows the swivel arm to rotate on the post, and a spring plunger and series of detents to lock the swivel arm in place for securing the medicine bottle and in place for withdrawing the medicine from the bottle by means of a syringe.

These and other aspects, features and advantages of the present invention will become apparent from the following detailed description taken in conjunction with the accompanying drawings.

BRIEF DESCRIPTION OF THE SEVERAL VIEWS OF THE DRAWINGS

FIG. 6 is a perspective view of the invention.

DETAILED DESCRIPTION OF THE INVENTION

Detailed embodiments of the present invention are disclosed herein. It is to be understood, however, that the disclosed embodiments are merely exemplary of the invention and that the invention may be embodied in various and alternative forms. Therefore, specified structural and functional details disclosed herein are not to be interpreted as limitations, but merely as a basis for the claims and as a representative basis for teaching one skilled in the art to variously employ the present invention.

Figure 1:
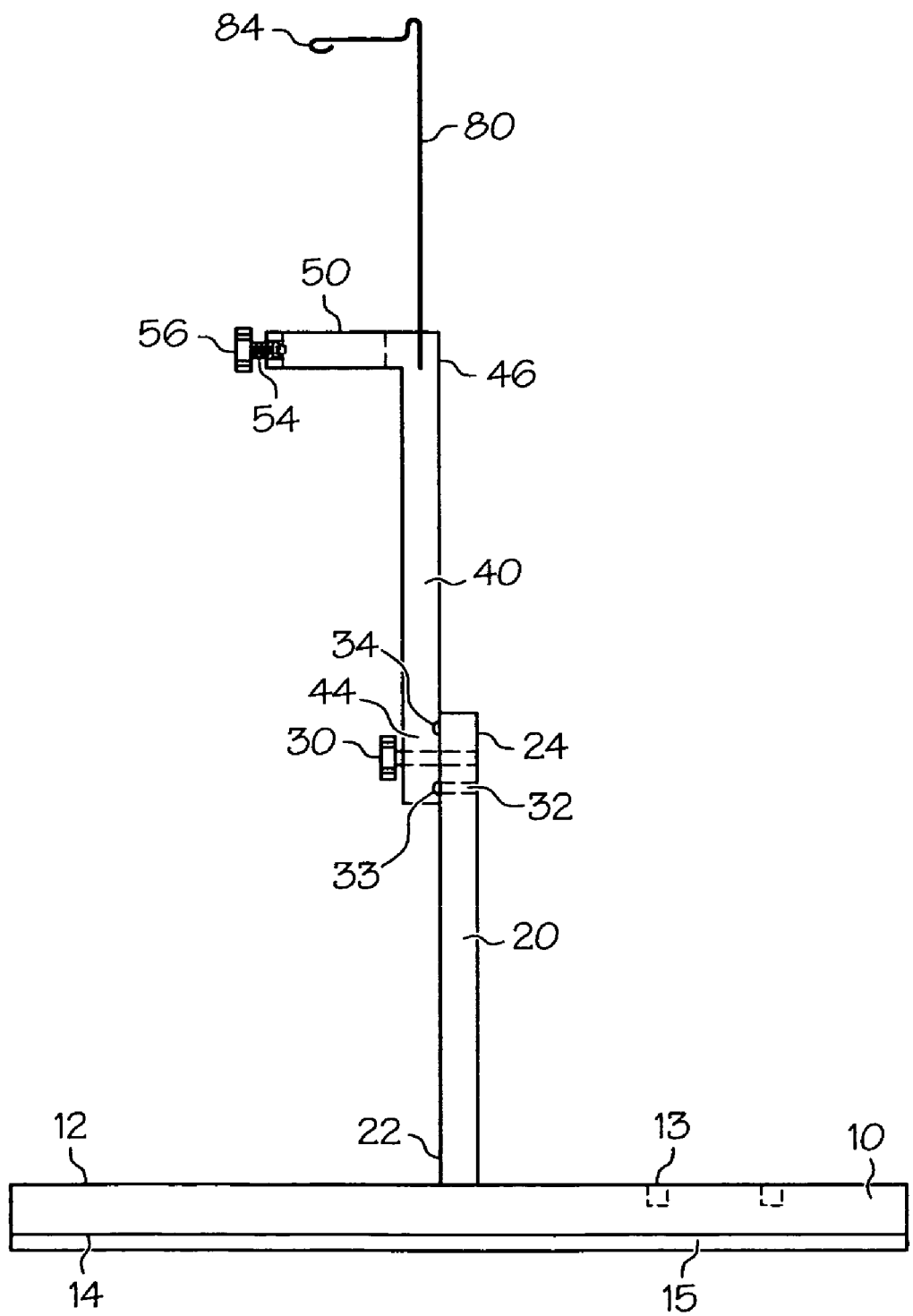
FIG. 1 is an elevation view of the front of the invention.

FIG. 1 is an elevation view of the front of the device. The invention comprises a base 10 having a top surface 12 and an underside 14. In the preferred embodiment the base 10 is a flat plate that measures approximately five (5) inches by five and one half (5½) inches, and as can be seen in FIG. 1 is substantially thinner than it is wide or deep. Aligned on the top surface 12 are a series of storage indents 13. The storage indents 13 are small holes in the top surface 12 of the base 10 that are sized to fit the needle stopper of a standard syringe. A needle stopper is a protective collar around the sharp needle of the syringe. Attached to the underside 14 of the base 10 is a pad 15. In the preferred embodiment, the pad 15 is made of "non-skid" rubberized matting material that prevents the device from sliding or moving when in use. In alternate embodiments the pad 15 can be of any type of material that would prevent slipping, including but not limited to rubber or soft plastics. In typical use the device will rest on a horizontal or nearly horizontal surface such as a table top or a counter top. The pad 15 prevents the device from moving, sliding or slipping while in use.

In the preferred embodiment the main components of the device, which include the base 10, the post 20, the swivel arm 40 and the flat hand 50, are made of stainless steel. In alternate embodiments the main components of the device could be made of any suitably sturdy and durable material, including but not limited to metals, plastics, or composites.

In the preferred embodiment the base 10 is approximately rectangular in shape. The shape of the base 10 has no bearing on the function of the device and could be in any shape. In alternate embodiments the base 10 could be replaced by a clamp or other device to removably attach the post 20 directly to a table top, a counter top, or any suitable horizontal surface. In yet other embodiments, the post 20 can be mounted directly on a suitable surface by any conventional means such as bolting, welding, gluing, or other well known means of attachment.

In the preferred embodiment the base has a front edge. A post 20 is attached approximately in the center of the front edge of the base 10. The post 20 extends upward, or approximately vertically, from the base 10. The post 20 has a bottom end 22 and a top end 24. In alternate embodiments the post 20 can be attached to any edge of the base 10. The bottom end 22 of the post 20 is attached to the base 10. The post 20 can be attached to the base 10 by any conventional means of attaching, such as bolting, welding or gluing. It is within the conception of the present invention that the post 20 and base 10 could be cast or molded from a single piece of material. In the preferred embodiment, the post 20 is made from a bar that is approximately one and one-half (1½) inch wide and a half (½) inch thick. The dimensions of the post 20 can vary substantially, as long as the post 20 is sufficiently rigid to support the swivel arm 40. In the preferred embodiment the post is approximately six inches long, but the length of the post can vary depending upon a number of factors, including the length of the syringes used in the device, or the configuration of the device in use on a horizontal surface.

At the top end 24 of the post 20 a swivel arm 40 is attached by a hinge 30. The swivel arm 40 has an elbow end 44 and a wrist end 46, and is attached to the post 20 at the elbow end 44. In the preferred embodiment, the hinge 30 is a screw mounted through the top end 24 of the post 20, and through the elbow end 44 of the swivel arm 40. The swivel arm 40 can rotate around the hinge 30. In alternate embodiments, the hinge 30 can be any conventional rotatable attachment, including but not limited to, a bolt, pin, or axle. In the preferred embodiment, the swivel arm 40 is made of the same half (½) inch by one and one-half (1½) inch bar as the post 20. In alternate embodiments the swivel arm 40 can be made from any suitably strong and durable material, including, but not limited to, metals, plastics, wood or wood based products. The only criteria is that the material be sufficiently strong and durable.

In the preferred embodiment the swivel arm 40 is approximately four and one-half (4½) inches long, but the length can vary depending upon the size of the syringe in use.

There is a spring plunger 32 mounted at the top end 24 of the post 20, near the hinge 30. Spring plungers are well known in the art, and contain a ball, typically made of steel, held in place by means of a spring. There is a corresponding aligned detent 33 in the elbow end 44 of the swivel arm 40, aligned so that the ball of the spring plunger 32 fits into the aligned detent 33, so that the swivel arm 40 can be locked into place when aligned with the post 20. In this configuration the swivel arm 40 extended directly upward from the post 20. With slight pressure on the swivel arm 40, the aligned detent 33 will slide off the spring plunger 32. The swivel arm 40 will turn around the hinge 30. When in use the swivel arm 40 will rotate outward and come to a rest when the askew detent 34 corresponds to the spring plunger 32.

There is a flat hand 50 attached at the wrist end 46 of the swivel arm 40. In the preferred embodiment, the flat hand 50 is made from the same material as the swivel arm 40. The flat hand 50 extends from the swivel arm 40 at a right angle. In the preferred embodiment, the flat hand 50 is approximately one and three-quarters (1¾) inches long. In alternate embodiments the flat hand 50 can be sized to accommodate various size medicine bottles. In the preferred embodiment, the flat hand 50 is attached to the swivel arm 40 by welding. The flat hand 50 can be attached to the swivel arm 40 in any conventional manner, including, but not limited to, welding, bolting, or gluing. It is within the conception of the invention that the flat hand 50 can be made from the same piece of material as the swivel arm 40 that had been bent at ninety degrees at the end, or is cast of a single piece in this configuration. When the swivel arm 40 is extended vertically upward and locked into place on the post 20 by means of the spring plunger 32 and the aligned detent 33 the flat hand 50 is approximately horizontal.

Figure 2:
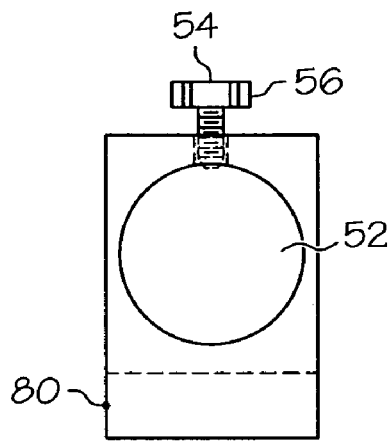
FIG. 2 is a detailed plan view of the flat hand element of the invention.
Figure 3:
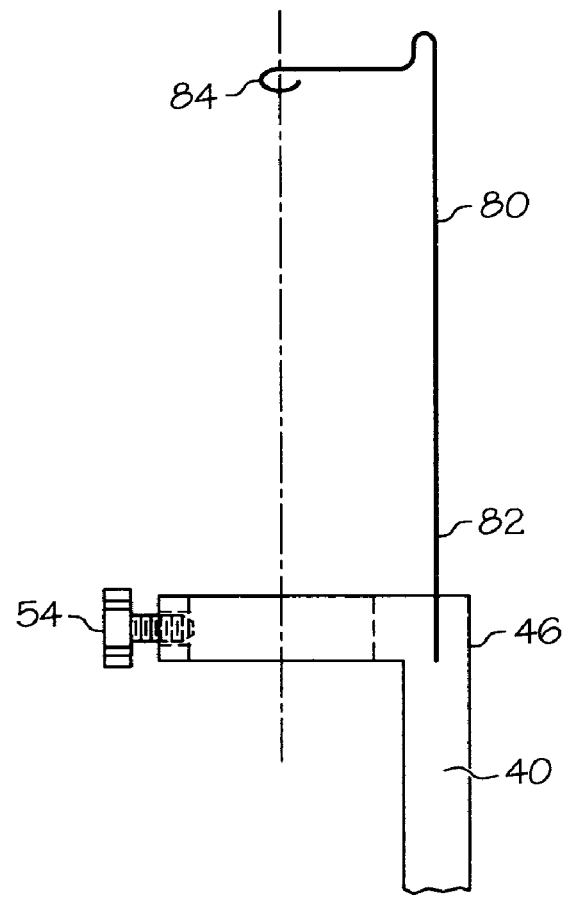
FIG. 3 is a detailed elevation view of the flat hand element of the invention.

As depicted in detail in FIGS. 2 and 3, there is a bottle recess 52 in the middle of the flat hand 50 that is designed to hold bottles of medicine. The invention is designed for use with conventional medicines, and these medicines typically come in bottles with diameters ranging from one-half (½) inch to approximately one and one-quarter (1¼) inches. In the preferred embodiment, the bottle recess 52 is bored out of the flat hand 50. In alternate embodiments the bottle recess 52 could be created by molding the flat hand 50 with the bottle recess 52 integrated. In the preferred embodiment the recess 52 extends through the flat hand 50.

There is a set screw 54 threaded from the edge of the flat hand 50 into the bottle recess 52 to hold bottles of medicine in place. There is a knob 56 at the end of the set screw 54 to allow a user to adjust the set screw 54 to secure the medicine bottle or bottle holder in to place within the recess 52.

In an alternate embodiment there is also a bottle holder to hold smaller vials or bottles of medicine. The outside diameter of the bottle holder is approximately the same as the inside diameter of the bottle recess 52, so that the bottle holder fits snugly into the bottle recess 52 and is held in place with the set screw 54. The bottle holder is comprised of a holder base with a holder collar that fits securely over the holder base. Smaller vials or bottles of medicine can be placed in the holder base and secured by the holder collar. The bottle holder serves the additional function of protecting vials or small bottles of medicine from breaking or being damaged by the set screw 54. It is within the conception of the invention that padding material, ranging from cotton wrap to plastics or rubberized materials, could also be used to secure the bottle of medicine within the bottle recess 52 and protect the bottle of medicine from the set screw 54.

In the preferred embodiment, the bottle holder is made out of PVC material. The inner diameter of the bottle holder is just slightly larger than the outer diameter of a standard bottle of insulin, so that the bottle of insulin can be snuggly slipped into the bottle holder. In the preferred embodiment there is padding placed in the bottom of the bottle holder to protect the bottle of insulin. In alternate embodiments, the bottle holder and the bottle recess 52 can be sized to hold any size bottle of medicine. With appropriate sizing, and with the use of a padding material within the recess 52 and on the end of the set screw 54, a bottle of medicine could conceivably by held within the recess 52 without the use of the bottle holder 60. In yet another embodiment, the bottle recess 52 could be lined with a padding or protective material to protect and secure a medicine bottle.

As shown in detail in FIG. 3, there is a syringe holder 80 attached to the wrist end 46 of the swivel arm 40 adjacent to the flat hand 50. In the preferred embodiment the syringe holder 80 is made from heavy gage wire, but it is conceivable that the syringe holder 80 could be made from any suitably material. The syringe holder 80 has an attachment end 82 and a curved finger 84.

In the preferred embodiment, the attachment end 82 of the syringe holder 80 is welded to the wrist end 46 of the swivel arm 40 near the flat hand 50. In alternate embodiments, the syringe holder 80 can be attached to the swivel arm 40 by any conventional means of attachment, including, but not limited to, welding, bolting or gluing. In another alternate embodiment, the syringe holder 80 can be attached to the swivel arm 40 by means of an attachment mount that would allow the syringe holder 80 to be adjusted in length to accommodate different size syringes. In yet another embodiment of the invention, the syringe holder 80 could be mounted in a hole sized to accommodate the attachment end 82 of the syringe holder 80, and drilled into the wrist end 46 of the swivel arm 40. Various holes would be drilled to allow the syringe holder 80 to accommodate different sized syringes. In this alternate embodiment, the attachment end 82 of the syringe holder 80 would have a right angle bend, allowing the attachment end 82 to be placed in one of the holes and the curved finger 84 to extend above the bottle recess 52. There would also be a clip to securely hold the syringe holder 80 in place.

Figure 4:
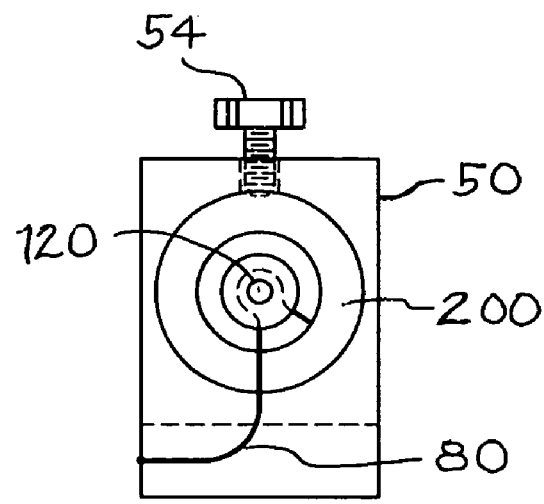
FIG. 4 is a detailed plan view of the flat hand with bottle and syringe.

As depicted in FIG. 3, the syringe holder 80 extends upward from the flat hand 50 when the flat hand 50 and swivel arm 40 are locked into place on the post 20. The end of the syringe holder 80 is bent into a curved finger 84 that extends over the bottle recess 52. The curved finger 84 is aligned approximately over the center of the bottle recess 54. As depicted in FIG. 4, the curved finger 84 can be curved from the front edge 16 of the base 10 back towards the center of the base 10.

In the preferred embodiment, the syringe holder 80 is approximately five inches long to accommodate standard small sized (100 cc) insulin syringes. In alternate embodiments the syringe holder 80 would be sized to accommodate any standard sized syringe or hypodermic needle.

Figure 5:
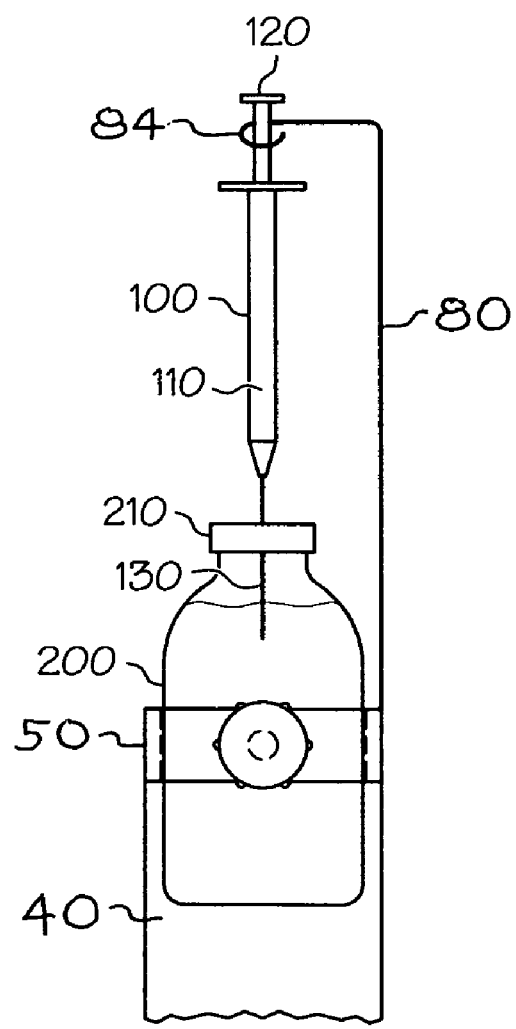
FIG. 5 is a detailed elevation view of the syringe holder with bottle and syringe.

The invention is designed to allow a user to fill a syringe with one hand. To use the invention, a medicine bottle 200 is placed in the bottle recess 52 and secured by means of the set screw 54, as shown in FIGS. 4 and 5. In an alternate embodiment, the medicine bottle is placed in the protective bottle holder, and the bottle holder is placed in the bottle recess 52 of the flat hand 50, and locked into place by means of the set screw 54.

The user can make ready a number of syringes 100 by placing them on the base 10 by inserting the needle stopper into the storage indents 13 of the base 10. One syringe 100 can be prepared by removing the needle stopper from the needle 130 of the syringe 100. The needle 130 is then stabbed into the Elastomeric seal 210 at the top of the medicine bottle 200. In this configuration, the syringe 100 will be extending upward approximately vertically, and the plunger 120 can be placed inside the curved finger 84 of the syringe holder 80 as depicted in FIGS. 4 and 5.

The swivel arm 40 is then swiveled outward and down as depicted in FIG. 6. As can be seen from this configuration, the curved finger 84 will hold the syringe 100 in place. This will nearly invert the flat hand 50, placing the medicine bottle 200 nearly upside down. The flat hand 50 will come to rest when the askew detent 34 locks into place on the spring plunger 32. This will place the curved finger 84 of the syringe holder 80 outward from the post 20 and base 10. The curved finger 84 will be holding the plunger 120, which will hold the syringe 100 in place.

In the preferred method of use of the invention, the base 10 is place at or near the edge of a horizontal surface such as a table or counter top. This will allow the flat hand to be extended past the edge of the surface, allowing the user easy access to the syringe 100. The user can then pull down on the plunger 120 with one hand in the same manner as a user with two hands would do. As shown in FIG. 5, the barrel 110 of the syringe 100 has a lip, and the curved finger 84 will hold the lip and prevent the syringe 100 from pulling out of the bottle. The user can then pull down on the plunger 120, thus creating a vacuum within the barrel 110 of the syringe 100, and sucking medicine out of the medicine bottle 200 and into the syringe 100. The user will fill the syringe 100 with more than the desired amount of medicine, then push the plunger 120 in, removing air and excess medicine from the barrel 110 of the syringe. The swivel arm 40 will then be swung back up and locked into position, and the full syringe is then ready for use. The process can be repeated if the user wants to fill more than one syringe for later use.

It is within the conception of the invention that the swivel arm 40 could be sufficiently short so that the user could place the base 10 of the invention anywhere on a flat surface, and have room to pull down on the plunger 120 of the syringe 100. It is also within the conception of the invention that the flat hand 50 could be rotatably mounted directly to the post 20, forgoing the swivel arm 40 completely.

The present invention is well adapted to carry out the objectives and attain both the ends and the advantages mentioned, as well as other benefits inherent therein. While the present invention has been depicted, described, and is defined by reference to particular embodiments of the invention, such reference does not imply a limitation to the invention, and no such limitation is to be inferred. The depicted and described embodiments of the invention are exemplary only, and are not exhaustive of the scope of the invention. Consequently, the present invention is intended to be limited only be the spirit and scope of the claims, giving full cognizance to equivalents in all respects.

I claim:

1. A one hand syringe filling device for filling a syringe with medicine from a medicine bottle, said one hand syringe filling device comprising:
   a base;
   a post mounted to said base;
   a swivel arm having an elbow end and a wrist end, said elbow end rotatably attached to said post such that said swivel arm rotates;
   a flat hand attached to said wrist end of said swivel arm such that when said swivel arm is rotated said flat hand is inverted;

a bottle recess within said flat hand, said bottle recess sized to accommodate a medicine bottle having an elastomeric seal;

a syringe holder having a curved finger attached to said wrist end of said swivel arm;

wherein said bottle recessed is configured to accommodate a medicine bottle containing medicine such that when said medicine bottle is placed in said bottle recess and a needle of a syringe having a syringe barrel and a syringe plunger is inserted into said elastomeric seal of said medicine bottle and said curved finger of said syringe holder hooks around said syringe plunger where it extends from said syringe barrel of said syringe, and said swivel arm is rotated on said swivel arm to invert said medicine bottle so that the medicine may be removed from said medicine bottle by said syringe.

2. The one hand syringe filling device of claim 1, wherein said syringe filling device is portable and wherein said base is flat plate having a non-skid lower surface.

3. The one hand syringe filling device of claim 2, wherein said flat plate includes a number of indents sized to accommodate a multiplicity of syringe needle stoppers.

4. The one hand syringe filling device of claim 1, wherein said syringe filling device is portable and wherein said base is a clamp for mounting said device.

5. The one handed syringe filling device of claim 1, wherein said swivel arm is attached to said post by means of a hinge.

6. The one hand syringe filling device of claim 1 wherein a set screw is threaded through said flat hand and into said bottle recess for securing said medicine bottle within said recess.

7. The one hand syringe filling device of claim 1 further comprising a spring plunger mounted in said post, and an aligned detent and an askew detent in said swivel arm, said spring plunger engaging said aligned detent to hold said swivel arm in a first position and said spring plunger engaging said askew detent to hold said swivel arm in a second position, wherein said first position maintains said flat hand is in a horizontal position and said second position maintains said flat hand is in an inverted position.

8. The one hand syringe filling device of claim 1 wherein said curved finger is sized to accommodate different sized syringe plungers, whereby said one hand syringe filling device can accommodate any sized syringe.

* * * * *